US00PP17605P3

(12) United States Plant Patent
Thomsen

(10) Patent No.: US PP17,605 P3
(45) Date of Patent: Apr. 17, 2007

(54) ***EUPHORBIA* PLANT NAMED 'HJOR048'**

(50) Latin Name: *Euphorbia milii Desmoul.×Euphorbia lophogona Lam.*
Varietal Denomination: HJOR048

(75) Inventor: Steen Thomsen, Sonderso (DK)

(73) Assignee: Hjortebjerg Plant Licence A/S, Sonderso (DK)

( * ) Notice: Subject to any disclaimer, the term of this patent is extended or adjusted under 35 U.S.C. 154(b) by 0 days.

(21) Appl. No.: 11/236,841

(22) Filed: Sep. 28, 2005

(65) Prior Publication Data

US 2006/0085880 P1 Apr. 20, 2006

(30) Foreign Application Priority Data

Oct. 15, 2004 (QZ) ..... PBR 20041909

(51) Int. Cl.
*A01H 5/00* (2006.01)

(52) U.S. Cl. ..... Plt./302
(58) Field of Classification Search ..... Plt./302
See application file for complete search history.

(56) References Cited

PUBLICATIONS

McLaughlin, A Word or Two About Gardening From Africa via Thailand Comes Some Low–Maintenance Garden Color, 2002, University of Florida IFAS Extension [online], [retrieved on Jun. 12, 2006]. Retrieved from the Internet <http://miami–dade.ifas.ufl.edu/programs/urbanhort/publications/A–Word–or–Two–II.htm>.4 pages.*

Upov–rom GTITM Plant Variety Database, 2006/01, GTI Jouve Retrieval Software, Citation for *Euphorbia* '2004–8', one page.*

* cited by examiner

*Primary Examiner*—Kent Bell
*Assistant Examiner*—June Hwu
(74) *Attorney, Agent, or Firm*—Foley & Lardner LLP

(57) ABSTRACT

A new distinct cultivar of *Euphorbia* plant named 'HJOR048', characterized by its compact, globular, upright plant habit; very dense and bushy plant form, mainly due to upright stems; large number of long stemmed flowers per plant due to 6 to 9 cm in length yellow-green peduncles, with gray-brown mottling towards base; striking color combinations of light red (pink) bracts (when opening RHS 36C, RHS 54A when fully opened) and staminate cyathia with yellow glands (RHS 9A) to green-yellow glands (RHS 1C) during development; and large, obovate, leaves (yellow-green, RHS 144A when young and green, RHS 137A when mature).

4 Drawing Sheets

Botanical designation: *Euphorbia milii* Desmoul.×*Euphorbia lophogona* Lam.
Variety denomination: 'HJOR048'.

BACKGROUND OF THE INVENTION

The present Invention relates to a new and distinct cultivar of *Euphorbia* plant, botanically known as *Euphorbia milii* Desmoul.×*Euphorbia lophogona* Lam., commonly known by the name Crown of Thorns, and hereinafter referred to by the name 'HJOR048'.

The new *Euphorbia* cultivar is a product of a planned breeding program conducted by the Inventor, Steen Thomsen, in Haarslev, Fyn, Denmark. The new *Euphorbia* cultivar originated from a cross made in November of 2003 by the Inventor between an unnamed, unpatented seedling plant of an *Euphorbia milii* Desmoul. cultivar and an unnamed, unpatented seedling plant of an *Euphorbia lophogona* cultivar. The Inventor selected the new *Euphorbia* cultivar as a single flowering plant from the progeny of the above crossing in January of 2004 on the basis of its flower color combination, large leaves and upright, compact plant habit. Plants of the new *Euphorbia* cultivar have upright, compact plant habit, and produce large, abundant inflorescence with pink floral bracts.

Asexual reproduction of the new cultivar was first performed in February of 2004 by terminal cuttings, and propagation in trial production batches in Hjortebjerg, Denmark, has demonstrated that the combination of unique features as disclosed herein for this new *Euphorbia* cultivar are firmly fixed and retained through successive generations of asexual reproduction. The new cultivar reproduces true-to-type.

BRIEF SUMMARY OF THE INVENTION

The following traits have been repeatedly observed and are determined to be the unique characteristics of 'HJOR048'. These characteristics in combination distinguish 'HJOR048' as a new and distinct *Euphorbia* cultivar:

1. Compact, globular, upright plant habit;
2. Very dense and bushy plant form, mainly due to upright stems;
3. Large number of long stemmed flowers per plant due to 6 to 9 cm in length yellow-green peduncles, with gray-brown mottling towards base;
4. Striking color combinations of light red (pink) bracts (when opening RHS 36C, RHS 54A when fully opened) and staminate cyathia with yellow glands (RHS 9A) to green-yellow glands (RHS 1C) during development; and
5. Large, obovate, leaves (yellow-green, RHS 144B when young and green, RHS 137A when mature).

Plants of the new *Euphorbia* cultivar 'HJOR048' differ from plants of the parental cultivars, an unnamed, unpatented seedling plant of an *Euphorbia milii* Desmoul. cultivar and an unnamed, unpatented seedling plant of an *Euphorbia*

*lophogona* Lam. cultivar, primarily by floral bract and leaf size and color. Plants of 'HJOR048' produce large, light red (pink) bracts on long peduncles and large, yellow-green leaves. In addition, plants of 'HJOR048' have more proliferate flowering and a longer flowering season than the parental cultivars.

Plants of the new *Euphorbia* cultivar 'HJOR048' can be compared to plants of the *Euphorbia milii* cultivar 'Eros', (patented, U.S. Plant Pat. No. 15,413). In side-by-side comparisons conducted by the Inventor in Haarslev, Denmark, plants of the new cultivar 'HJO048' and the comparison cultivar 'Eros' differ in the following characteristics:

1. Plants of 'HJOR048' are shorter, wider and more compact (length about 13 cm, spread about 22 cm), than plants of 'Eros' (height about 15 cm; spread about 17 cm);
2. Plants of 'HJOR048' have striking color combinations of light red (pink) bracts (when opening RHS 36C and RHS 54A when fully opened) and staminate cyathia with yellow glands (RHS 9A) to green-yellow glands (RHS 1C) during development, whereas plants of 'Eros' have bright red bracts (when opening RHS 42B and RHS 45C when fully opened) and staminate with cyathia orange glands (RHS N25A) to red glands (RHS 43C) during development;
3. Plants of 'HJOR048' produce about 100 to 120 flowers and bud per plant and about 6 to 8 flowers open per week per plant, whereas plants of 'Eros' produce about 60 flowers and buds per plant and about 1 to 4 flowers open per week per plant;
4. Plants of 'HJOR048' produce few lateral branches whereas plants of 'Eros' are freely branching, and the lateral branches of 'HJOR048' are shorter and thinner (length about 3 cm, width about 4 cm) than lateral branches of 'Eros' (length about 6 cm, width about 6.5 mm);
5. Plants of 'HJOR048' produce less leaves per lateral branch (about 7) than plants of 'Eros' which produce about 10 leaves per lateral branch, and the leaves of 'HJOR048' are longer and wider (length about 10 cm, width about 40 mm) than leaves of 'Eros' (length about 7 cm, width about 30 mm); and
6. Plants of 'HJOR048' have longer and sturdier peduncles (6 to 9 cm) than plants of 'Eros' (3 to 4 cm).

BRIEF DESCRIPTION OF THE PHOTOGRAPHS

The accompanying color photographs illustrate the overall appearance and details of flower form, color and structures of the new cultivar 'HJOR048', showing the colors as true as it is reasonably possible to obtain in color reproductions of this type. Colors in the photographs may differ slightly from the color values cited in the detailed botanical description, which more accurately describe the actual colors of the new *Euphorbia* cultivar.

DETAILED BOTANICAL DESCRIPTION

Figure 1:
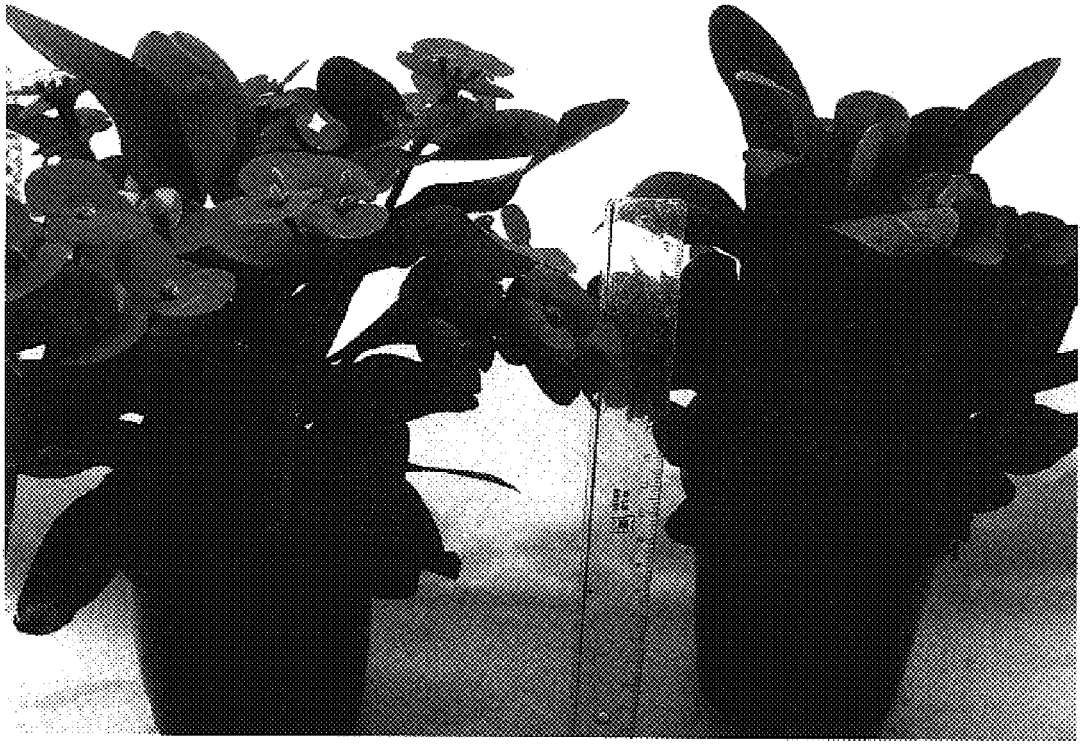
FIG. 1 shows a side view perspective comparing a typical, potted flowering plant of the new cultivar 'HJOR048' (one the left) to a typical, potted flowering plant of the comparison cultivar 'Eros' (on the right), both grown in 11 cm pots.
Figure 2:
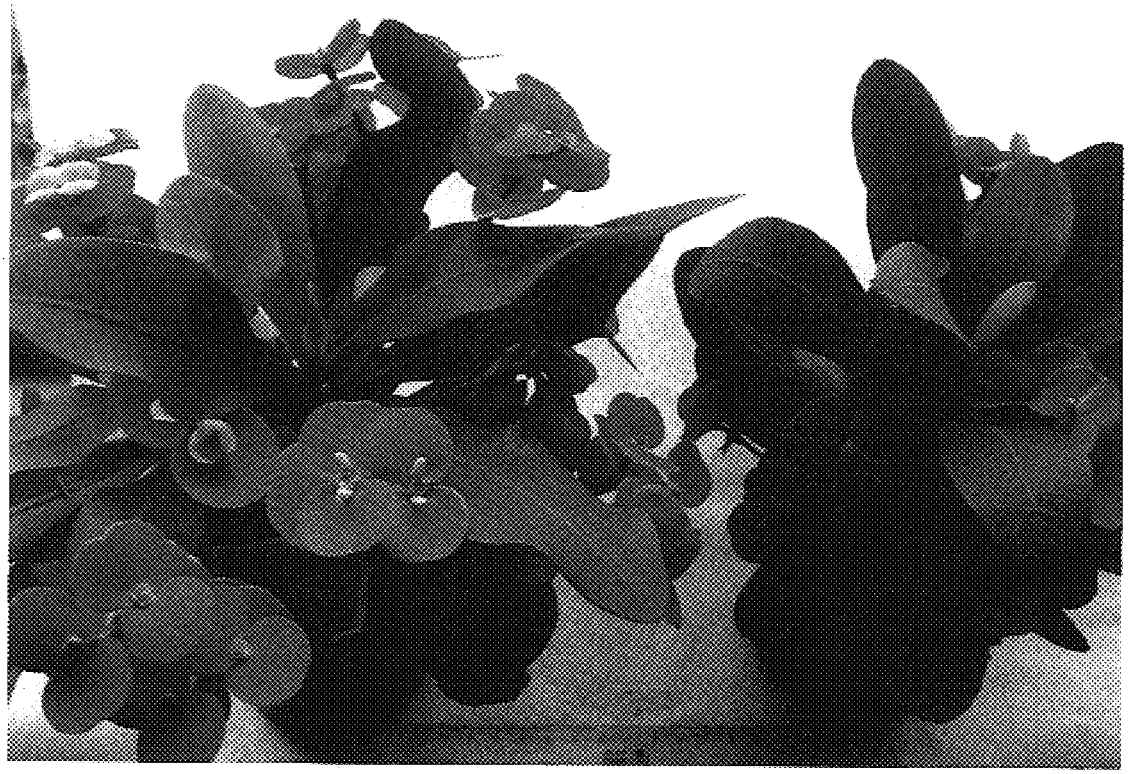
FIG. 2 shows a top view perspective comparing a typical, potted flowering plant of the new cultivar 'HJOR048' (one the left) to a typical, potted flowering plant of the comparison cultivar 'Eros' (on the right), both grown in 11 cm pots.
Figure 3:
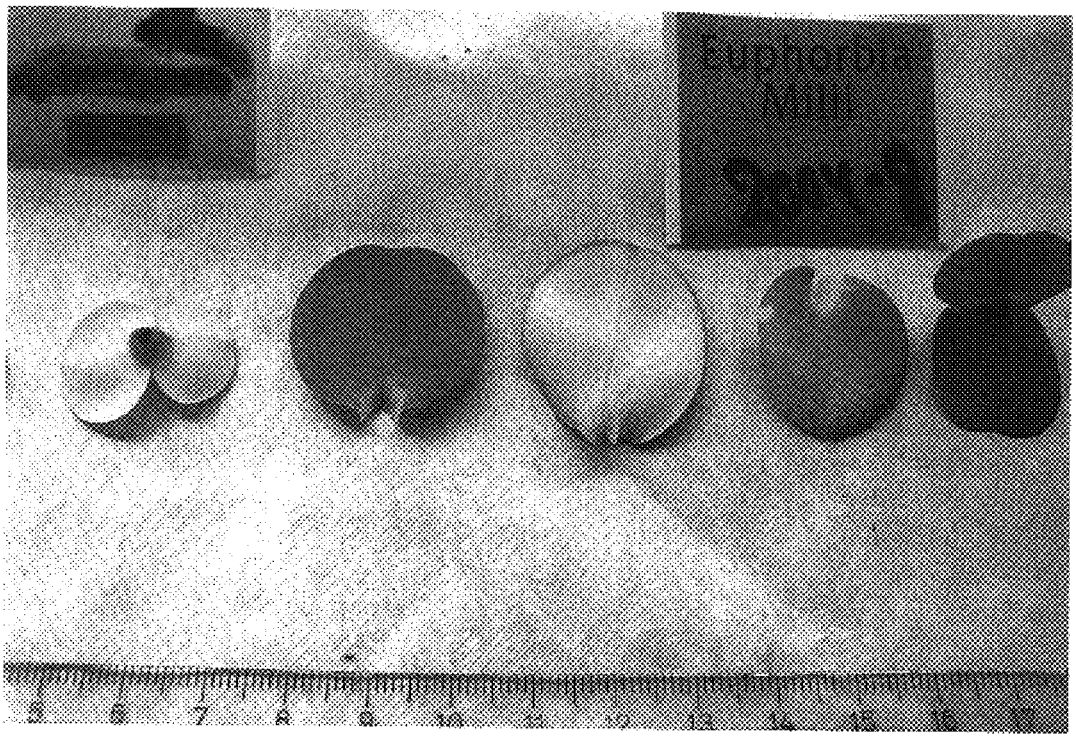
FIG. 3 shows a close-up view of young and mature floral cymes of a typical flowering plant of the new cultivar 'HJOR048'.
Figure 4:
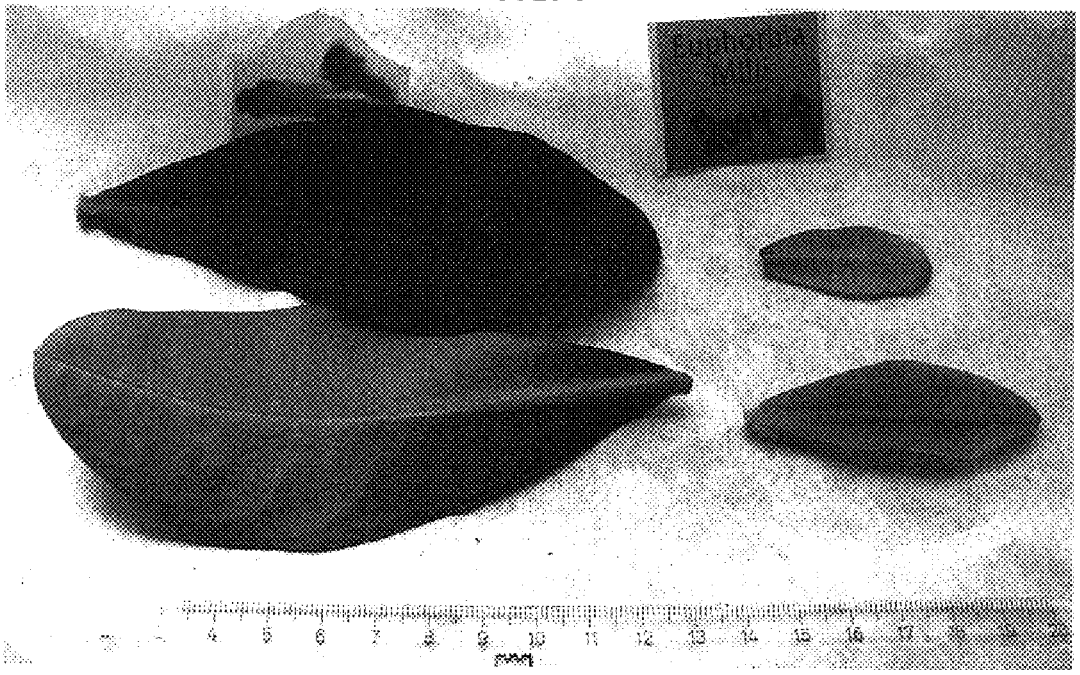
FIG. 4 shows a close-up view of different size leaves of a typical flowering plant of the new cultivar 'HJOR048'.

Plants of the new *Euphorbia* cultivar 'HJOR048' have not been observed under all possible environmental conditions. The phenotype may vary somewhat with variations in environment such as temperature, light intensity, day length, and fertility level without, however, any variance in genotype.

The aforementioned photographs, together with the following observations, measurements and values describe plants of the new cultivar 'HJOR048' as grown in a glass greenhouse in Fyn, Denmark, under conditions which closely approximate those generally used in commercial practice. Plants of 'HJOR048' were grown in a greenhouse with the day temperature range of 21° C. to 24° C. and the night temperature range of 20° C. to 21° C. Plants of 'HJOR048' were grown in full light, and no photoperiodic treatments or growth retardants were used. For flower induction, plants of 'HJOR048' are subjected to high irradiance conditions and a constant temperature of 24° C.

Color references are made to The Royal Horticultural Society Colour Chart (R.H.S.), $4^{th}$ edition, except where general terms of ordinary dictionary significance are used. Plants used for this description were grown for about 17 weeks after cutting and produced in 6 cm pots. Other pot sizes can be used and the plants are intended for indoor use or as a bedding plant in temperate climates while it is a perennial garden plant in tropical and subtropical areas.

Botanical classification: *Euphorbia milii* Desmoul.× *Euphorbia lophogona* Lam.

Parentage:

*Female or seed parent.*—Unnamed, unpatented seedling plant of *Euphorbia milii* Desmoul.

*Male or pollen parent.*—Unnamed, unpatented seedling plant of *Euphorbia lophogona* Lam.

Propagation:

*Type cutting.*—Terminal vegetative cuttings taken from plants kept in the vegetative stage by shading and high temperatures (25° C.)

*Time to initiate roots.*—About 10 to 14 days at 18° C. to 21° C. in tunnels in a greenhouse.

*Root description.*—Fine, fibrous, well branched.

*Root color.*—Gray-white, RHS 157C.

Plant description:

*Form.*—Perennial plant with upright plant habit. 'HJOR048' flowers in cymes with 5 cyathia subtended by 5 glands and 2 colored bracts.

*Crop time.*—After rooting, about 16 to 18 weeks are required to produce finished flowering plants in 11 cm pots.

*Vigor.*—Moderately vigorous growth rate.

*Plant size.*—Height (soil level to top of plant plane): About 13 cm. Width: About 22 cm.

*Lateral branches.*—Freely branching with about 3 lateral flowering branches forming at every node; dense and bushy. Lateral branches measure between 3 to 5 cm in length and about 5 mm in diameter. Internode length measures about 8 mm. About 2 to 4 buds per lateral stem and about 4 to 6 flowers per lateral stem. Stems are square to pentagonal with thorned ridges — about 15 mm thick at the base. Aspect of stem is upright, with lateral branches at about 45°. Young stem color is yellow-green, RHS 144A, and gray-green, RHS 197A. By each node appears a group of thorns: 1 large (1 cm) and 2 to 4 small (2 to 4 mm). Young thorns are soft and gray-purple, RHS 187B with gray-green base, RHS 191B, while the older thorns becomes stiffer and change color to gray-brown, RHS N199B.

*Foliage description.*—Leaves alternate, single, obovate in shape, entire margin and pinnate venation. Length: About 10 cm. Width: About 40 mm. Apex: Rounded. Base: Cuneate. Texture: smooth, waxy, dull, and glabrous. Color: Young foliage: (upper side): Yellow-green, RHS 144B; (under side): Yellow-green, RHS N144D. Mature foliage: (upper side): Yellow-green, RHS 137A; (under side): Yellow-green (uniform), RHS 144B. Venation pattern: Pinnate. Venation color: (upper side): Yellow-green, RHS 144B; (under side): Yellow-green, RHS 144C. Petiole length: About 3 mm. Petiole diameter: About 2 mm. Petiole color: Yellow-green, RHS 144C.

Flower description:

*Flower arrangement and shape.*—Floral arrangements composed of dichasial cymes. The flowers (cyathia) are reduced so only a gland and the reproductive organs are present. Subtending the cyathia are two colored bracts. The flowers are further complicated by the unique feature of cone to funnel shaped floral buds appearing at the base of the bracts in two or more layers.

*Natural flowering season.*—Continuous throughout the spring and summer in subtropical and tropical regions. In colder climates season, can be extended by greenhouse production with high temperatures and supplementary irradiance.

*Flower longevity on the plant.*—About 5 to 9 weeks. However, longevity of individual flowers is highly dependent on temperature and light conditions. Bracts turn green with age. Entire cymes drop after withering.

*Quantity of flowers and buds per plant.*—About 100 to 200.

*Rate of flower opening.*—About 6 to 8 per week.

*Fragrance.*—None.

*Inflorescence size.*—Diameter: About 6×8 cm. Height: 10 to 12 cm.

*Buds.*—Cone to funnel shape, measures about 7 mm in length and about 6 mm in diameter, color: gray-yellow, between RHS 160C to RHS 160D.

*Flowers.*—Round shape, upright aspect, about 5 mm in diameter and about 1 mm in height (depth).

*Bracts.*—2, opposite, partly overlapping at base, ovoid to inverted cordate shape with obcordate tip, about 17 mm in length and about 24 mm in width, color when opening: (upper side) light red (pink), RHS 36C; (underside) pale yellow-green, RHS 150D, color when fully opened: (upper side): light red (pink), RHS 54A; (under side) light red-purple, RHS 65D, with red-purple edges, RHS 67C, color fading to red-purple, RHS 61D, mottled with yellow-green, RHS 149B to RHS 149C.

*Glands.*—Flower (cyanthium) subtended by 5 conspicuous glands. Color from yellow, RHS 9A to green-yellow, RHS 1C during development.

*Peduncles.*—Length measuring from 6 to 9 cm, diameter measuring about 4 mm, angle about 45°, strong in strength, color: yellow-green, RHS 144A, with base mottled gray-brown, RHS N 199C.

*Pedicel.*—Length measuring from 2 to 3 cm, diameter measuring about 3 mm, angle about 45°, strong in strength, color: yellow-green, RHS 144A, with base mottled gray-brown, RHS N 199C.

Reproductive organs:

*Androecium.*—Stamen: 5 (appears after flower matures).

*Anthers.*—Globular shape measuring about 1 to 2 mm, yellow-orange color, RHS 15A.

*Pollen.*—Plentiful, yellow-orange color, RHS 15A.

*Gynoecium.*—Pistil: Appears before cyathia mature; one, tripartite pistil measuring about 2 mm in length; stigma tripartite with split ends, and color RHS 1C, greenish-yellow; style measuring about 1 to 3 mm in length and color, RHS 1D, greenish-yellow; ovary color, RHS 149D, yellow-green.

*Seeds/fruit.*—None observed.

*Weather tolerance.*—Plants of the new *Euphorbia* cultivar have exhibited good tolerance to drought, rain and wind; however, flowering may cease during cold and dark periods when temperatures are below +15° C.

*Pest/disease tolerance/susceptibility.*—Plants of the new *Euphorbia* cultivar have exhibited good tolerance to following fungi: powdery mildew and *Thielaviopsis* (a root rot fungus). Also, they appear to be less infected by Thrips (*Frankliniella*).

I claim:

1. A new and distinct cultivar of *Euphorbia* plant named 'HJOR048', as illustrated and described herein.

* * * * *